United States Patent [19]
Lambrecht et al.

[11] 4,011,307
[45] Mar. 8, 1977

[54] PRODUCTION OF $^{203}$Pb-TRIS-HYDROXYMETHYL AMINO METHANE

[75] Inventors: Richard M. Lambrecht, East Quogue; Samuel Packer, Manhasset, both of N.Y.; Jerald C. Merrill, Salt Lake City, Utah; Harold L. Atkins; Alfred P. Wolf, both of Setauket, N.Y.; Patrick R. Bradley-Moore, New York, N.Y.

[73] Assignee: The United States of America as represented by the United States Energy Research and Development Administration, Washington, D.C.

[22] Filed: June 3, 1976

[21] Appl. No.: 692,625

[52] U.S. Cl. .................................. 424/1; 176/11; 250/303; 424/9; 423/249
[51] Int. Cl.$^2$ ................. A61K 29/00; A61K 43/00; G01T 1/161; G21H 5/02
[58] Field of Search .............. 424/1, 1.5, 9; 176/11, 176/16; 250/303; 423/249

[56] References Cited

UNITED STATES PATENTS 3,957,963   5/1976   Salmon et al. ..................... 424/1

OTHER PUBLICATIONS

Syed, Chemical Abstracts, vol. 82, No. 7, Feb. 17, 1975, p. 175, Abstract No. 40162d.
Safi et al., Medical Radioisotope Scintigraphy, vol. II, International Atomic Energy Agency, Vienna 1973, pp. 497–518.
Merrill, International Journal of Applied Radiation and Isotopes, vol. 24, No. 12, Dec. 1973, pp. 701–702.

Primary Examiner—Benjamin R. Padgett
Assistant Examiner—Christine M. Nucker
Attorney, Agent, or Firm—Dean E. Carlson; Leonard Belkin

[57] ABSTRACT

$^{203}$Pb-tris complex injected for use in the detection and localization of tumors. The lead-203 is produced from the deuteron bombardment of a thallium target and chemically separated from the thallium. The tris is added which complexes with the lead-203.

5 Claims, No Drawings

PRODUCTION OF $^{203}$Pb-TRIS-HYDROXYMETHYL AMINO METHANE

BACKGROUND OF THE INVENTION

This invention was made under or during the course of a contract with the United States Energy Research and Development Administration.

Up to the present time phosphorous-32 has been employed most frequently as an agent for the detection and localization of eye tumors. This radioisotope has a fourteen day one-half life of pure beta emission. The patient's radiation dose is thus high and the efficacy is marginal. Studies show that the use of this agent is only about 80% effective, that is, in about 20% of eye removals, the eye was found to be normal.

As a result of the foregoing, there has been considerable interest, without success up to now, in the discovery or development of other radiopharmaceuticals which could be more effectively employed in tumor detection and localization, especially malignant eye melanoma.

SUMMARY OF THE PRESENT INVENTION

Lead-203 ($^{203}$Pb) is a radioactive nuclide that has excellent physical characteristics appropriate for tumor scanning. It has a short half-life, 52.1 hours, and decays by electron capture with the emission of a high abundance (95 percent) of 279 keV photons, and the absence of any beta radiation. The tissue penetration of its photon radiation is sufficient for localization of deep-seated tumors, specifically posteriorly located choroidal melanoma. The successful use of this isotope would obviate the necessity for invasive techniques of localization. A low uptake by the retina implies that there would be little background interference, while a low uptake by the lens would indicate the safety of the radionuclide with regard to the induction of a radiation cataract.

There have been reported previous attempts to use lead as a possible agent for the treatment of tumors but these attempts apparently failed to produce useful results due to the toxicity of lead in the bloodstream.

We have discovered that when lead-203, near carrier-free in stable nonradioactive lead, is complexed with tris as a carrier that the toxicity effects from the presence of lead in the blood stream are avoided or minimized to an extent that would no longer interfere with the use of this radioisotope.

By tris herein is meant tris-hydroxymethyl amino methane, or, by IUPAC nomenclature, 2-amino-2-hydroxymethyl, 1, 3-propanediol.

In accordance with the principles of this invention, there is provided a method of preparing carrier-free lead-203 tris comprising the steps of exposing a target of naturally occurring thallium to a deuteron beam having an energy of greater than about 11 but not in excess of 22.7 MeV, said target being of sufficient thickness along the path of the beam so as to cause said beam to be degraded to about 11 MeV in the thallium for a sufficient length of time to produce lead-203 by the reaction $^{203}$Tl(d,2n) $^{203}$Pb, dissolving the target, chemically separating said $^{203}$Pb from the dissolved target, and dissolving the $^{203}$Pb in an aqueous solution of tris, the latter being supplied in sufficient amount to adjust the solution to a pH in the range of about 6.8 to 7.2. The nuclear reaction requires an energy of at least 4.02 MeV but degradation to about zero MeV is required in order to compensate for the effect of the presence of the support for the thallium. The range of 22.7 MeV down to about 11 MeV is dictated by efficiency considerations.

In another preferred embodiment there is provided a tumor detection and localizing agent consisting of a sterile, carrier free aqueous solution of lead-203 tris having a pH in the range of about 6.8 to 7.2.

In another preferred embodiment of this invention there is provided a method of detecting and localizing a tumor such as eye melanoma comprising the step of injecting an aqueous, sterile solution of the complex, carrier-free lead-203 tris having a pH in the range of about 6.8 to 7.2.

It is thus a principal object of this invention to provide for the improved detection and localization of certain tumors, especially eye melanoma.

Other objects and advantages of this invention will hereinafter become obvious from the following description of preferred embodiments of this invention.

DESCRIPTION OF THE PREFERRED EMBODIMENTS

The lead-203 is produced using the $^{203}$Tl(d,2n) $^{203}$Pb nuclear reaction by bombarding a target of naturally occurring thallium with deuterons at an initial energy of greater than 11 but not in excess of 22.7 MeV. The target should be of sufficient thickness in the direction of the deuteron beam so that all deuteron energy will be expended in the target, that is, the deuteron beam will be degraded to about 11 MeV in the thallium.

The target is then removed from the target area and the lead-203 is chemically separated therefrom. Chemical separation involves the steps of dissolving the target with sulfuric acid, adding a $Fe^{3+}$ carrier, and adding ammonium hydroxide until the Fe precipitates as the hydroxide. The lead is present as a co-precipitate of the iron. The precipitate is removed and washed and then dissolved in nitric acid followed by co-precipitation of the iron and lead. This is repeated several times as required to reduce the level of thallium to non-toxic levels (the thallium remains in solution and does not precipitate with the iron and lead).

In order to separate the lead-203 from the iron, the precipitate is dissolved in a reagent which is very selective to remove iron. Such a reagent is methylisobutylketone-isoamylocetate, and when it is added and shaken vigorously, an aqueous layer appears which is removed and heated to dryness. Nitric acid is added and this may be repeated as often as required. After heating to dryness a small solid residue consisting of lead-203 nitrate remains.

It has been found that the separation process as described above gives about 90% in radiochemical yield, and in excess of 99.99% radionuclidic purity.

The lead-203 tris complex is made by adding an aqueous solution of tris to the nitrate in sufficient amount to produce a pH in the range of about 6.8–7.2. The pH could also be adjusted to this range if desired by adding solutions of sodium hydroxide or nitric acid. After filtering, the solution is ready for injection, provided sterile pyrogen-free conditions have been maintained throughout.

Extensive studies of the lead-203 tris complex show that it has the ability to localize in melanomas, especially those of the eye.

The $^{203}$Pb-tris as described herein was injected in a relatively large number of mice and hamsters which were tumor bearing animals. After injection all animals were studied for tissue distribution and it was concluded that there was selective uptake by the tumors of the $^{203}$Pb.

Certain hamsters with eye melanoma were injected as noted above and visualized after 24 hours using a conventional gamma camera. Results from one such group of hamsters are given in Table I showing distribution of the lead-203 tris in percent uptake per gram of tissue at various times. These results as well as others demonstrate feasibility of the use of lead-203 tris for the clinical localization of certain tumors including eye melanoma.

A more comprehensive description in the use of this complex to detect and localize tumors appears in the paper "Localization of Radioactive Lead in Ocular and Skin Melanoma" appearing in *Investigative Ophthalmology*, June 1975, pp 492–494.

EXAMPLE

The following is a summary based upon procedures developed and successfully carried out:

1. Name of drug: Lead-203 tris-hydroxymethyl aminomethane ($^{203}$Pb-tris) for intravenous administration.
2. List of components:
   a. Sterile water for injection U. S. P. (Travenol Laboratories, Deerfield, Ill.)
   b. "Near carrier-free" lead-203 complexed with tris-hydroxymethyl aminomethane.
      1. Chemical analysis of the tris-hydroxymethyl amino as indicated by the supplier:

|      |   |           |
|------|---|-----------|
| Pb   | < | 0.001%    |
| Fe   |   | 0.00005%  |
| Ca   |   | 0.00003%  |
| Mg   |   | 0.00005%  |
| B, As | — | not detected |

2. Chemical analysis of the thallium metal (by the supplier) used for the target indicates:

|        |   |         |
|--------|---|---------|
| Tl     |   | 99.998% |
| Pb     |   | 11 ppm  |
| Cu     |   | 4 ppm   |
| Ag     | < | 5 ppm   |
| others |   | 1 ppm   |

BNL analysis for Pb indicated 10 ppm.

3. Quantitative Composition: 203Pb-lead tris. Chemical analysis (typical) of the 203 Pb-tris preparation analyzed after radioactive decay of the $^{203}$Pb.

|    |   |                                   |
|----|---|-----------------------------------|
| Fe | < | 0.1 μg                            |
| Tl | 3 | −24 μg                            |
| Pb |   | 10 μg per gram of target material |

Lead-203 decays by electron capture with a half-life of 52.1 hours. The principle gamma photons are 279 keV (95%) and 401 keV (5%) characteristic thallium X-rays are present

| Radionuclidic purity: | > | 99.99% $^{203}$Pb |
|---|---|---|
| Specific activity: | | 1 mCi $^{203}$Pb-tris/ml |
| | | 0.08–0.24 × 10$^{-4}$ moles tris/ml |
| | | pH = 6.6–7.5 |

4. Source and preparation of components used:
   a. Lead-203 (Chemistry Department, Brookhaven National Laboratory, Upton, New York 11973).
   b. Tris-hydroxymethyl amino methane [2-2mino-2-hydroxymethyl, 1, 3-propanediol] (Ultra-pure Reagent, Schwarz/Mann, Orangeburg, New York).
   c. Sterile water for injection, U. S. P. (Travenol Laboratories, Deerfield, Illinois).
   d. Thallium (99.998% purity, rod ⅝ inch, Alpha Inorganics, Beverly, Massachusetts).
   e. Sodium hydroxide (Fisher Scientific Company, certified 6.25 N (25%), Fairlawn, New Jersey).
   f. Ammonium hydroxide (Mallinckrodt, approx. 58%, Analytical reagent, St. Louis, Missouri).
   g. Nitric acid (Mallinckrodt, approx. 70%, Analytical reagent, St. Louis, Missouri).
   h. Sulfuric acid (B & A, reagent A. C. S., Allied Chemicals, Morristown, New Jersey).
   i. Ferric nitrate (Certified reagent, Fisher Scientific Company, Fairlawn, N. Y.)
   j. Hydrochloric acid (Baker Analytical Reagent, Phillipsburg, Pennsylvania).
   k. Methylisobutylketone (4 methyl 2 pentanone, Eastman Kodak, Rochester, N. Y.).
   l. Isoamylacetate (Certified Reagent, Fisher Scientific Company, Fairlawn, N. J.).

All glassware used in the final steps of radiopharmaceutical formulation is prewashed in a concentrated sulfuric acid bath, rinsed with pyrogen-free water, and dried at 180° for 3 hours. These procedures are performed on the day of, or the day before production and formulation.

5. Methods and facilities used for manufacturing:
   a. *Nuclide Production:* The lead-203 was produced on the BNL 60 inch cyclotron using the $^{203}$Tl (d,2n) $^{203}$Pb nuclear reaction with the deuterons degraded from 22.7 → 0 MeV in a target of 99.998% purity thallium metal. The chemical separation of the lead-203 from the irradiated target was about 90% in radiochemical yield, and in excess of 99.99% radionuclidic purity.
   b. *Chemical Separation Procedure to be Followed:* The irradiated thallium target is placed into a 40 ml centrifuge tube, and 5.0 ml of concentrated sulfuric acid is added to affect dissolution. Then water (pyrogen-free) is added to increase the total volume to 10–20 ml. Add 1.0 ml Fe$^{3+}$ carrier iron nitrate (10 mg/ml). Add concentrated ammonium hydroxide until the Fe precipitates as the hydroxide.

Centrifuge and decant the supernatant to radioactive waste. Wash the precipitate twice with about 10 ml of 3M ammonium hydroxide, centrifuging and decanting each time. Dissolve the precipitate with about 1 ml of concentrated nitric acid and 1 M nitric acid as required. If any residue does not dissolve, decant the supernatant to another 40 ml centrifuge tube. Again reprecipitate the Fe$^{+3}$, centrifuge, decant and wash twice with 3M ammonium hydroxide as before. Repeat the steps again, beginning dissolution in nitric acid. After the precipitate is washed twice as in the previous steps, it is dissolved in 10 ml of 8 M HCl and transferred to a 60 ml separatory funnel. Add 2.5 ml of methylisobutylketone-isoamylacetate (1-1) and shake vigorously for precisely one minute. Allow the layers to separate and withdraw the organic layer with a Pasteur capillary pipet. Repeat the extraction procedure three times. Withdraw the aqueous layer to a 50 ml beaker, add a teflon stirring bar and take to dryness on a hot plate. Add 10 ml of concentrated nitric acid and cover with a watch glass until fumes of $NO_x$ cease evolving. Remove the watch glass and evaporate to dryness. Repeat the procedure, as required, beginning with the addition of 10 ml $HNO_3$ if a crystalline residue develops.

c. *Radiopharmaceutical Formulation:* Lead-203 tris was prepared by the addition of an aqueous solution of 2-amino-2-hydroxymethyl, 1, 3-propanediol to the near carrier-free lead-203. The solution is adjusted to pH 6.8-7.2, by addition of the tris. Only if required 3.12 N sodium hydroxide or 1 M nitric acid are used to adjust the pH. The solution was passed through a presterilized $0.22\mu$ millipore filter (to assure sterility) and directly into a sterile, pyrogen-free multi-injection vial.

d. Assay and Calibration Procedures:

1. Radionuclidic purity-$^{203}$Pb is identified by analysis of the gamma-ray spectrum by multichannel pulse height analysis, utilizing a Ge(Li) detector. Each preparation is checked.
2. Chemical Analysis: Performed after radioactive decay of $^{203}$Pb by atomic absorption and x-ray fluorescence spectrometry for determination of Pb, Tl and Fe.
3. Thin layer chromatography: Cellulose using (isopropanol: chloroform ammonium hydroxide) (3:1:1). The tris has an $R_f$ of 0.6.
4. Before administration to the patient the radioactivity is measured with a well-type ionization chamber (Capintec Radioisotope Calibrator).
5. Sterility and Pyrogenicity by adhering to good manufacturing practices throughout, starting with the last part of the chemical procedure, and beginning with the steps entitled radiopharmaceutical formulation. Sterile water for injection is used for the preparation of reagents and washing purposes. All glassware is first washed in sulfuric acid bath followed by thoroughly rinsing in pyrogen-free water and then drying at 180° for 3 hours. Samples will be routinely assayed for sterility and pyrogenicity by independent outside laboratories. A millipore 0.22 $\mu$m filter is used to remove particulate matter and assure sterility of the radiopharmaceutical.

The thallium present in the target should be pure, by which is meant that there are no detectable amounts of interfering products present, as is understood in the art.

TABLE I

Distribution of Carrier-Free Lead-203 Tris in Percent Uptake per Gram of Tissue at Various Times*

| Tissue | Time | | | | | |
|---|---|---|---|---|---|---|
| | 1 | 3 | 6 | 24 | 72 | 144 |
| Melanoma-Eye | 1.048 | 0.976 | 1.609 | 1.314 | 0.724* | 0.821 |
| | ±0.214 | ±0.190 | ±0.306 | ±0.188 | ±0.260 | ±0.150 |
| Normal-Eye | 0.200 | 0.086 | 0.111 | 0.054 | 0.084 | 0.047 |
| | ±0.037 | ±0.010 | ±0.011 | ±0.006 | ±0.005 | ±0.007 |
| Melanoma-Skin | 1.095 | 1.051 | 1.209 | 0.845 | 1.010 | 0.749 |
| | ±0.132 | ±0.137 | ±0.154 | ±0.075 | ±0.154 | ±0.068 |
| Normal-Skin | 0.401 | 0.256 | 0.286 | 0.090 | 0.122 | 0.071 |
| | ±0.055 | ±0.055 | ±0.058 | ±0.009 | ±0.018 | ±0.008 |
| Cornea | 0.834 | 0.173 | 0.891 | 0.200 | 0.084* | 0.062 |
| | ±0.269 | ±0.102 | ±0.717 | ±0.059 | | |
| Lens | 0.017 | 0.023 | 0.021 | 0.005 | 0.006* | 0.005 |
| | ±0.013 | ±0.012 | ±0.017 | ±0.006 | | |
| Vitreous | 0.031 | 0.028 | 0.036 | 0.031 | 0.014* | 0.018 |
| | ±0.016 | ±0.007 | ±0.015 | ±0.012 | | |
| Retina | 0.169 | 0.074 | 0.251 | 0.206 | 0.091* | 0.127 |
| | ±0.106 | ±0.007 | ±0.132 | ±0.002 | | |
| Choroid | 1.109 | 0.950 | 0.337 | 0.361 | 0.127* | 0.131 |
| | ±0.631 | ±0.855 | ±0.163 | ±0.103 | | ±0.124 |
| Kidney | 25.32 | 18.156 | 17.703 | 10.508 | 17.443 | 3.904 |
| | ±2.55 | ±1.205 | ±2.069 | ±0.481 | ±1.766 | ±0.217 |
| Liver | 5.463 | 4.273 | 7.188 | 3.729 | 4.841 | 2.331 |
| | ±0.721 | ±0.350 | ±0.701 | ±0.346 | ±0.398 | ±0.457 |
| Gonads | 2.076 | 0.238 | 0.663 | 0.164 | 0.135 | 0.079 |
| | ±1.017 | ±0.041 | ±0.142 | ±0.029 | ±0.020 | ±0.004 |
| Brain | 0.107 | 0.067 | 0.135 | 0.139 | 0.067* | 0.109 |
| | ±0.025 | ±0.006 | ±0.123 | ±0.019 | ±0.008 | ±0.010 |
| Muscle | 0.159 | 0.100 | 0.090 | 0.026 | 0.041 | 0.027 |
| | ±0.024 | ±0.020 | ±0.015 | ±0.003 | ±0.005 | ±0.011 |
| Blood | 3.870 | 3.635 | 5.847 | 3.007 | 3.792 | 0.852 |
| | ±0.749 | ±0.404 | ±0.828 | ±0.267 | ±0.224 | 0.175 |
| Bone | 3.977 | 3.991 | 5.320 | 5.342 | 9.761 | 5.757 |
| | ±0.648 | ±0.641 | ±0.717 | ±0.758 | ±2.016 | ±0.602 |
| Intestines | 0.841 | 0.653 | 1.593 | 1.664 | 2.064* | 0.217 |
| | ±0.238 | ±0.111 | ±0.265 | ±0.457 | ±0.597 | ±0.095 |

*Averages and standard deviations for an average of 8–17 hamsters per time group, except * data which represents results from 4 animals.

What is claimed is:
1. The method of preparing carrier-free $^{203}$Pb-lead tris-hydroxymethyl amino methane comprising the steps of:
a. exposing a target consisting of naturally occurring thallium to a beam of deuterons of at least about 11 MeV but not in excess of 22.7 MeV energy, said target being of sufficient thickness along the path of said beam so as to cause said beam to be de- graded down to about 11 MeV in the thallium, for a sufficient length of time to produce lead-203 by the reaction $^{203}Tl\ (d,\ 2n)\ ^{203}Pb$;

b. dissolving said target;

c. chemically separating said $^{203}Pb$ in the form of $^{203}Pb$-nitrate from the dissolved target; and d. dissolving the $^{203}Pb$-nitrate in an aqueous solution of tris-hydroxymethyl amino methane, the latter being supplied in sufficient amount to adjust the solution to a pH in the range of about 6.8 to 7.2.

2. The method of claim 1 in which $^{203}Pb$ is separated from the dissolved target by adding a $Fe^{3+}$ carrier followed by precipitating out the iron compound with 203 Pb-nitrate as a coprecipitate, and then separating the 203 Pb-nitrate from the iron compound by dissolving the latter in the precipitate leaving said 203 Pb-nitrate.

3. The method of claim 2 in which the target is dissolved in sulfuric acid and the iron compound precipitated out is iron hydroxide as a result of the addition of ammonium hydroxide to the solution containing $Fe^{3+}$ carrier.

4. The tumor detection and localizing agent consisting of a sterile, carrier-free aqueous solution of lead-203 tris-hydroxymethyl amino methane having a pH in the range of about 6.8 to 7.2.

5. The method of detecting and localizing a tumor such as eye melanoma comprising the step of injecting an aqueous, sterile solution of the complex, carrier-free lead-203 tris-hydroxymethyl amino methane having a pH in the range of about 6.8 to 7.2.

* * * * *